US012478415B2

(12) United States Patent
Zenker et al.

(10) Patent No.: US 12,478,415 B2
(45) Date of Patent: Nov. 25, 2025

(54) CLAVICLE SEGMENTAL PLATE SYSTEM

(71) Applicant: DEPUY SYNTHES PRODUCTS, INC., Raynham, MA (US)

(72) Inventors: Martin Zenker, Zuchwil (CH); André Galm, Basel (CH); Martin Bammerlin, Basel (CH); Marcel Schweizer, Zuchwil (CH); Arabella Fontana, Zuchwil (CH); Daniel Andermatt, Möhlin (CH); Simon Lambert, London (GB); Stefan Nijs, Leuven (BE); Harry Hoyen, Cleveland, OH (US); Martin Jaeger, Freiburg im Breisgau (DK); Chunyan Jiang, Beijing (CN)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 18/641,944

(22) Filed: Apr. 22, 2024

(65) Prior Publication Data

US 2024/0268872 A1 Aug. 15, 2024

Related U.S. Application Data

(60) Continuation of application No. 17/452,532, filed on Oct. 27, 2021, now Pat. No. 11,992,251, which is a (Continued)

(51) Int. Cl.
*A61B 17/80* (2006.01)

(52) U.S. Cl.
CPC ...... *A61B 17/8061* (2013.01); *A61B 17/8014* (2013.01)

(58) Field of Classification Search
CPC . A61B 17/80; A61B 17/8004; A61B 17/8014; A61B 17/8023; A61B 17/8052; A61B 17/8057; A61B 17/8061
See application file for complete search history.

(56) References Cited

U.S. PATENT DOCUMENTS 5,718,705 A * 2/1998 Sammarco ......... A61B 17/8863 606/280
8,118,848 B2 * 2/2012 Ducharme ......... A61B 17/8061 606/291

(Continued)

FOREIGN PATENT DOCUMENTS

CA 2691279 7/2011
CA 2 983 488 10/2016

(Continued)

OTHER PUBLICATIONS

Synthes, "Clavicle Hook Plate, Technique Guide"; Synthes Catalog 2003, 7 sheets.

(Continued)

*Primary Examiner* — Eric S Gibson
(74) *Attorney, Agent, or Firm* — Fay Kaplun & Marcin, LLP

(57) ABSTRACT

A medial plate for treating fractures along a clavicle, comprising a plate body including a longitudinal component extending from a first end to a second end and an extension extending from the second end, the second end configured to be mounted over a medial head, a first set of variable angle holes extending through a portion of the longitudinal component including the second end of the longitudinal component and the extension, each of the first set of variable angle holes extending through the plate body along a central axis so that a bone screw is insertable therethrough at a user-selected angle relative to the central axis, and a plurality of combination holes extending through the longitudinal component, each of the plurality of combination holes includes a first portion configured to receive a bone screw at a user-selected angle and a second portion configured to receive a compression screw.

23 Claims, 10 Drawing Sheets

Related U.S. Application Data division of application No. 16/673,655, filed on Nov. 4, 2019, now Pat. No. 11,207,111.

(56) References Cited

U.S. PATENT DOCUMENTS

| | | | | |
|---|---|---|---|---|
| 9,072,556 | B2 | 7/2015 | Fritzinger et al. | |
| 9,486,262 | B2 | 11/2016 | Andermahr et al. | |
| 9,545,276 | B2 | 1/2017 | Buchanan et al. | |
| 10,265,112 | B2 | 4/2019 | Fritzinger et al. | |
| 10,631,903 | B2 * | 4/2020 | Govey | A61B 17/8004 |
| 10,687,854 | B2 | 6/2020 | Zenker et al. | |
| 10,881,438 | B2 * | 1/2021 | Govey | A61B 17/72 |
| 11,134,862 | B2 | 10/2021 | Crawford et al. | |
| 11,207,111 | B2 | 12/2021 | Zenker et al. | |
| 11,357,554 | B2 * | 6/2022 | Govey | A61B 17/72 |
| 11,786,144 | B2 | 10/2023 | Crawford et al. | |
| 11,857,229 | B2 * | 1/2024 | Govey | A61B 17/72 |
| 2007/0185493 | A1 * | 8/2007 | Feibel | A61B 17/8061 606/71 |
| 2010/0217327 | A1 * | 8/2010 | Vancelette | A61B 17/8061 606/281 |
| 2011/0184414 | A1 * | 7/2011 | Andermahr | A61B 17/809 606/281 |
| 2011/0224671 | A1 | 9/2011 | Koay et al. | |
| 2011/0264149 | A1 * | 10/2011 | Pappalardo | A61B 17/8019 606/86 R |
| 2012/0059424 | A1 | 3/2012 | Epperly et al. | |
| 2013/0090688 | A1 * | 4/2013 | Montello | A61B 17/7049 606/246 |
| 2013/0172948 | A1 * | 7/2013 | Fritzinger | A61B 17/8863 606/86 R |
| 2014/0172020 | A1 | 6/2014 | Gonzalez-Hernandez | |
| 2014/0277176 | A1 * | 9/2014 | Buchanan | A61B 17/8057 606/280 |
| 2015/0223851 | A1 * | 8/2015 | Hill | A61B 17/8061 606/281 |
| 2016/0310185 | A1 * | 10/2016 | Sixto | A61B 17/808 |
| 2016/0374742 | A1 | 12/2016 | Fritzinger et al. | |
| 2017/0100181 | A9 | 4/2017 | Fritzinger et al. | |
| 2018/0161081 | A1 * | 6/2018 | Anding | A61B 17/8605 |
| 2018/0256220 | A1 | 9/2018 | Koay et al. | |
| 2018/0256221 | A1 * | 9/2018 | Koay | A61B 17/7037 |
| 2018/0256223 | A1 | 9/2018 | Lueth et al. | |
| 2018/0256224 | A1 * | 9/2018 | Govey | A61B 17/8085 |
| 2018/0256226 | A1 * | 9/2018 | Govey | A61B 17/8061 |
| 2018/0344356 | A1 * | 12/2018 | Zenker | A61B 17/8061 |
| 2019/0076174 | A1 * | 3/2019 | Tiongson | A61B 17/846 |
| 2019/0076177 | A1 * | 3/2019 | Tiongson | A61B 17/8014 |
| 2019/0142304 | A1 * | 5/2019 | Crawford | A61B 34/25 606/281 |
| 2019/0269443 | A1 * | 9/2019 | Laird, Jr. | A61B 17/848 |
| 2019/0269446 | A1 * | 9/2019 | Laird, Jr. | A61B 17/8014 |
| 2021/0128210 | A1 * | 5/2021 | Zenker | A61B 17/8014 |
| 2021/0386322 | A1 | 12/2021 | Crawford et al. | |
| 2022/0071673 | A1 | 3/2022 | Zenker et al. | |

FOREIGN PATENT DOCUMENTS

| | | |
|---|---|---|
| CN | 202027696 | 11/2011 |
| CN | 105012000 | 11/2015 |
| CN | 105361939 | 3/2016 |
| CN | 107007342 | 8/2017 |
| CN | 207084848 | 3/2018 |
| CN | 207561971 | 7/2018 |
| CN | 208784886 | 4/2019 |
| JP | 3146826 | 12/2008 |
| JP | 2013-504390 | 2/2013 |
| JP | 2018-513752 | 5/2018 |
| JP | 2018-149297 | 9/2018 |
| WO | 2017/035302 | 3/2017 |
| WO | 2018/222449 | 12/2018 |

OTHER PUBLICATIONS

Synthes, “3.5 mm LCP Clavicle Hook Plates; Part of the Synthes locking compression plate (LCP) system”; Synthes Catalog 2007, 24 sheets.

* cited by examiner

CLAVICLE SEGMENTAL PLATE SYSTEM

PRIORITY CLAIM

The present application is a Continuation of U.S. patent application Ser. No. 17/452,532 filed on Oct. 27, 2021; which is a Divisional application of U.S. patent application Ser. No. 16/673,655 filed on Nov. 4, 2019, now U.S. Pat. No. 11,207,111. The disclosure of which is incorporated herewith by reference.

BACKGROUND

Fractures along a clavicle are quite common and may occur along any portion of the bone. Current implants are designed for treating only certain portions of the clavicle. For example, there is currently no practical implant dedicated to treating medial clavicular fractures. In addition, in some cases, existing clavicle plates may be poorly suited to a patient=s specific anatomy, creating soft-tissue irritation which may lead to pain and/or early removal of the plate.

SUMMARY

The present disclosure relates to a medial plate for treating medial fractures of a clavicle, comprising a plate body sized and shaped to be positioned along a medial portion of a clavicle bone. The plate body includes a longitudinal component extending from a first end to a second end along a longitudinal axis and an extension extending from the second end, away from the longitudinal axis, the second end configured to be mounted over a medial head of a clavicle bone, the plate body defined via an upper surface which, in an operative position, faces away from the clavicle bone, and a lower surface which, in the operative position, faces toward the clavicle bone. A first set of variable angle holes extend through a portion of the longitudinal component including the second end of the longitudinal component and the extension, each of the first set of variable angle holes extending through the plate body from the upper surface to the lower surface along a central axis so that a bone screw is insertable therethrough at a user-selected angle relative to the central axis of each of the first set of variable. A plurality of combination holes extends through the longitudinal component, laterally of the first set of variable angle holes, each of the plurality of combination holes includes a first portion configured to receive a bone screw at a user-selected angle relative to a central axis thereof and a second portion configured to receive a compression screw.

The present disclosure also relates to a method for treating a clavicular fracture, comprising identifying a location of a fracture relative to one of five sections of a clavicle bone to be treated, and determining a plate type for treating the fracture based on the identified location of the fracture.

BRIEF DESCRIPTION

DETAILED DESCRIPTION

Figure 1:
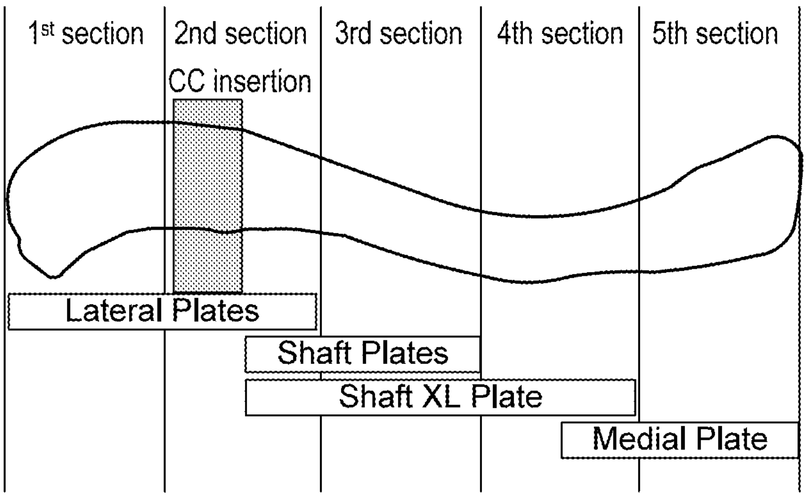
FIG. 1 shows a schematic drawing of a bone for a fracture-specific clavicle treatment system according to an exemplary embodiment of the present disclosure.

The present disclosure may be understood with reference to the following description and the appended drawings, wherein like elements are referred to with the same reference numerals. The present embodiments relate to the treatment of clavicular fractures and, in particular, relate to a clavicle osteosynthesis system for the treatment of lateral, mid-shaft and medial clavicle fractures, mal-unions and non-unions. Exemplary embodiments describe a fracture-specific plate system including multiple plates, each of which is designed to address a specific subset of fractures. Each of the bone plates is specifically sized, shaped and configured to treat a specific portion of the clavicle and is available in multiple shapes to correspond to clavicles of various sizes based upon a patient=s stature (e.g., height). For example, larger patients will require longer and/or larger plates than proportionally smaller patients. It will be understood by those of skill in the art that the terms lateral and medial, as used herein, are intended to refer to a lateral and medial direction, respectively, relative to a clavicle bone.

As shown in FIG. 1, according to a clavicle osteosynthesis system of the present disclosure, a clavicle may be divided into sections so that fractures along each of the sections may be treated using at least one plate provided by the system. In other words, each plate type is designed to address a specific subset of fractures. The clavicle extends from a lateral end to a medial end and may be divided into fifths defining five sections of equal lengths (designated as section 1-section 5) from the lateral to the medial end. Fractures occurring in the first section (i.e., a lateral-most section of the bone) may be treated using one of lateral plates 100-300 while fractures occurring in the fifth section (i.e., a medial-most section) may be treated using a medial plate 800. Fractures occurring in the third section (i.e., middle portion of the clavicle) may be treated using one of shaft plates 400-700.

The second and fourth sections, however, may be treated using one of lateral plates 100-300 or the medial plate 800, and shaft plates 400-700 depending on a specific location of the fracture. For example, a fracture occurring in the second section may be treated using one of lateral plates 100-300 or shaft plate 400-700, depending on a fracture location. A fracture occurring in the fourth subsection may be treated using one of shaft plates 400-700 or the medial plate 800, depending on a fracture location. These dedicated plate solutions are available in multiple shapes so that the plate best suited for a patient=s specific anatomy may be selected.

Figure 2:
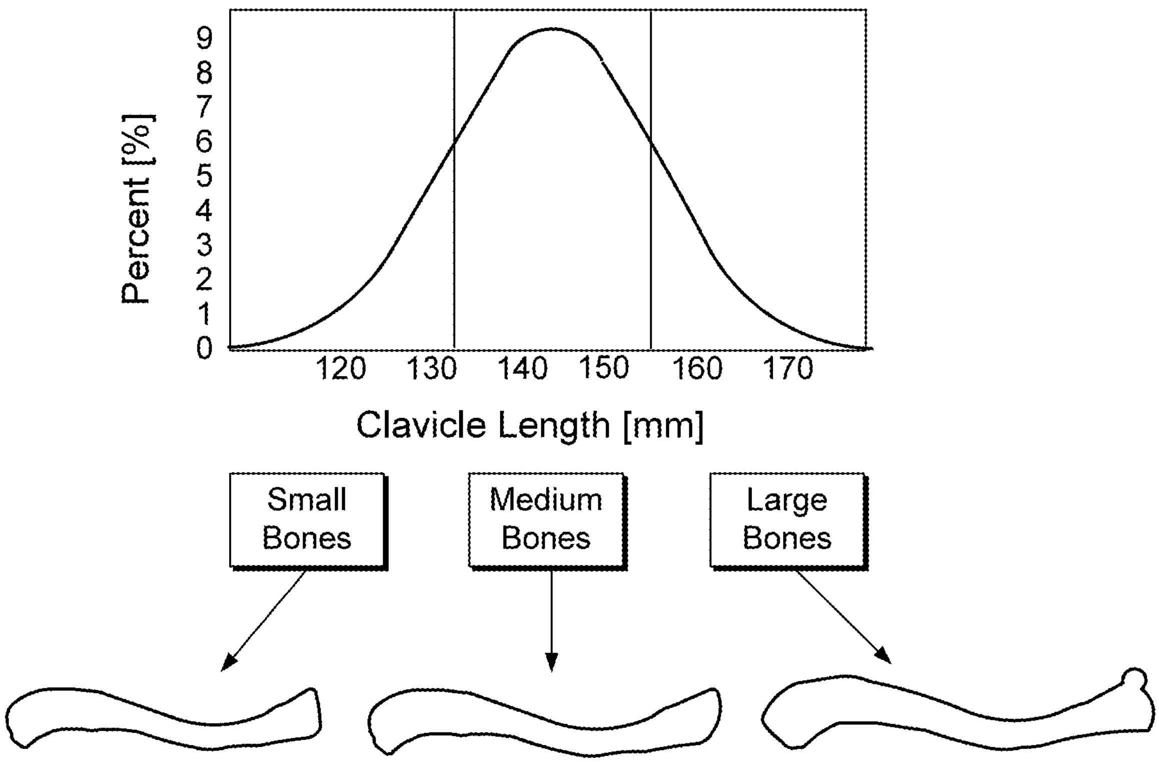
FIG. 2 shows an exemplary table including data for identifying optimal dimensions for plates included in the system of FIG. 1.
Figure 3:
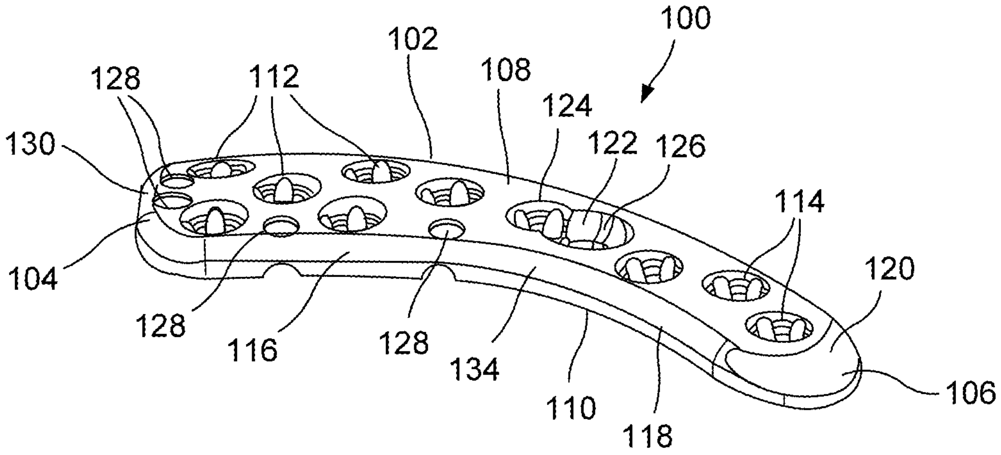
FIG. 3 shows a perspective view of a first lateral plate according to the system of FIG. 1.
Figure 4:
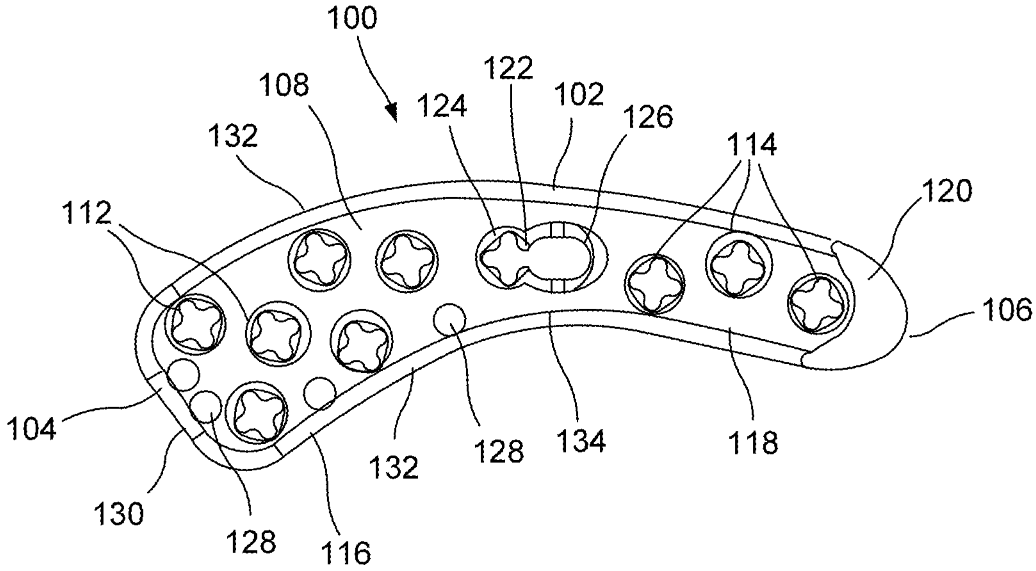
FIG. 4 shows a top plan view of the first lateral plate of FIG. 3.
Figure 5:
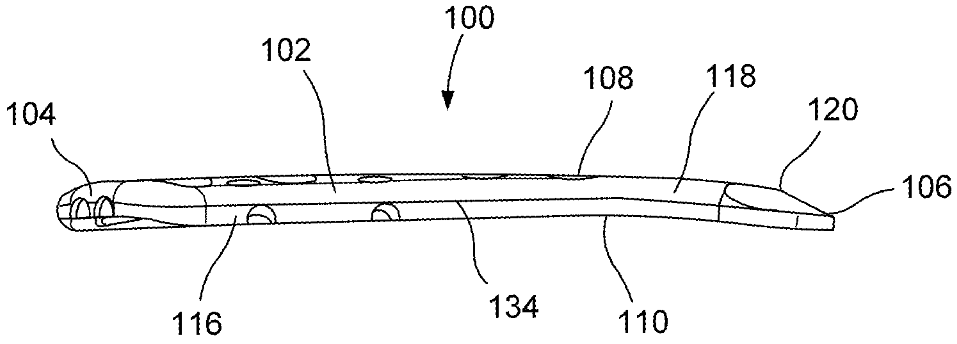
FIG. 5 shows a side view of the first lateral plate of FIG. 3.

As shown in FIG. 2, an exemplary embodiment including a database of clavicle bones of patients of varying stature was compiled and analyzed to determine optimal sizes, shapes and configurations of the lateral, shaft and medial plates described herein. In particular, in one embodiment, bone sizes were divided into three categories generally designated small, medium and large populations. Small bones included clavicles having lengths below 134 mm. Medium bones included clavicles having lengths ranging from 134 to 155 mm. Large bones included clavicles having lengths of over 155 mm. Using dimensions of the bones of the compiled data, polynomial equations were used to determine optimal transversal and coronal curvatures along with plate lengths for varying shapes of plates that would best fit patients of varying statures.

Lateral plates 100-300 according to the system of the present disclosure may be available in, for example, three sizes to account for differences in length and curvature of the clavicle based on a patient=s stature. For example, patients of smaller stature will have smaller clavicle bones with smaller dimensions, but stronger curvatures compared to a clavicle bone of a patient of larger stature. In one embodiment, coronal and/or transversal curvature and/or plate length of each of the lateral plates 100-300 may correlate to a patient=s height. Dimensions of the lateral plates 100-300 described below have been determined based on analysis of bones of patients of a variety of sizes. A physician or other user may select one of the three lateral plates 100-300 based on a size of the patient and a location of the fracture along a lateral portion of the clavicle.

As shown in FIGS. 3-9, a first lateral plate 100 according to an exemplary embodiment of the present disclosure comprises a plate body 102 extending from a first end 104 to a second end 106 and including an upper surface 108 which, when the first lateral plate 100 is in an operative position, faces away from a clavicle, and an inner, bone-facing surface 110 which, when the first lateral plate 100 is in the operative position, faces toward the clavicle. In the operative position, the first end 104 will be positioned over a lateral end of the clavicle so that plate body 102 extends along a superior surface of the clavicle along a length thereof corresponding to the first section and at least a portion of the second section of the clavicle, as described above with respect to FIG. 1, with the second end 106 extending toward a medial end of the clavicle. The first lateral plate 100, which is the smallest of the three lateral plates 100-300 to be described herein, may be selected by the user to treat small clavicles with very lateral, simple fractures. As will be described in further detail below, the first lateral plate 100 includes a plurality of variable angle holes 112, 114 extending through portions of the plate body 102 in a configuration selected to optimally treat lateral clavicle fractures.

The plate body 102 extends longitudinally along a curve corresponding to a curve along a lateral portion of the clavicle and has a width (i.e., a distance between longitudinal sides 132 of the plate body 102) which decreases from the first end 104 to the second end 106. The plate body 102 may also be curved to extend longitudinally about the clavicle. In one embodiment, the plate body 102 has a length ranging from approximately 40 mm to 70 mm. In another embodiment, the plate body 102 has a length ranging from approximately 45 mm to 65 mm and, in a more specific embodiment, the plate length ranges from approximately 50 mm to 60 mm. In one embodiment, the plate body 102 includes a radius of curvature ranging between 40 mm to 50 mm and, in one particular embodiment, includes a radius of curvature of approximately 44 mm. A width of the plate body 102 according to this embodiment ranges at the first end 104 from approximately 10 mm to 20 mm and, in a more particular embodiment ranges from approximately 15 mm to 16 mm. In one embodiment, the first end 104 is curved to extend about a lateral head of the clavicle. The second end 106 may include an angled surface 120 connecting the upper surface 108 to the lower surface 110, with the angled surface 120 angled to reduce a profile of the plate body 102 at the second end 106 to facilitate percutaneous insertion. In one embodiment, the angled surface 120 may extend at an angle extending between 10 and 30 degrees. In one example, the angled surface 120 may extend at an angle of approximately 20 degrees relative to the lower surface 110.

In one embodiment, the first lateral plate 100 includes a plurality of variable angles holes 112 extending through a first portion 116 of the plate body 102 proximate the first end 104. Each of the variable angle holes 112 extends through the plate body 102 from the upper surface 108 to the lower surface 110. In the operative configuration, the first portion 116 is configured to extend over a lateral fragment of the clavicle. Each of the variable angle holes 112 extends through the plate body 102 along a central axis and is configured to receive a bone screw therethrough at a user-selected angle within a permitted range of angulations relative to the central axis, as shown via the triangles in the cross-sections of FIGS. 6, 7 and 8. In one embodiment, the first portion 116 includes six variable angle holes extending therethrough, the variable angle holes 112 positioned relative to one another to maximize the number of screws that may be inserted therethrough into the lateral fragment.

Figure 6:
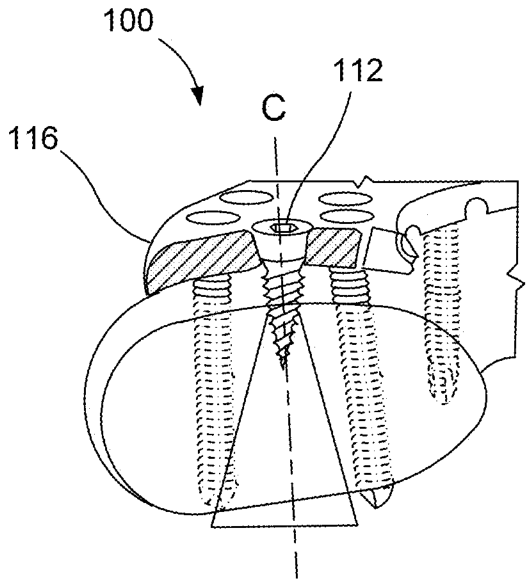
FIG. 6 shows a cross-sectional perspective view of a lateral portion of the first lateral plate of FIG. 3.

In one example, two of the variable angle holes 112 are positioned along a longitudinal axis of the plate body 102. As shown in FIG. 6, central axes of these holes extend along a central plane C extending perpendicularly through the longitudinal axis of the plate body 102 relative to the upper surface 108. Two of the variable angle holes 112 in this embodiment are positioned proximate a lateral edge 130 of the plate body 102 on opposing sides of the longitudinal axis and in a lateral direction relative to a lateral-most one of the holes 112 along the longitudinal axis.

Figure 7:
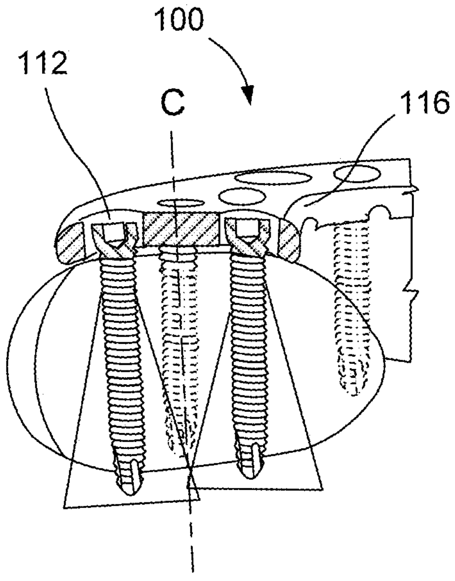
FIG. 7 shows another cross-sectional perspective view of a lateral portion of the first plate of FIG. 3.

As shown in FIG. 7, the central axes of one or more of these variable angle holes 112 may converge toward the central plane C at an angle of approximately 5 degrees so that the central axes intersect the central plane at a point distal of the lower surface 110. In one embodiment, a posterior one of the variable angle holes 112 shown in FIG. 7 extends along a central axis that converges toward the central plane C while an anterior one of the variable angle holes 112 shown in FIG. 7 extends along a central axis that extends substantially parallel to the central plane C. Two of the variable angle holes 112 are, in this embodiment, positioned on opposing sides of the longitudinal axis, between the two holes 112 along the central axis.

Figure 8:
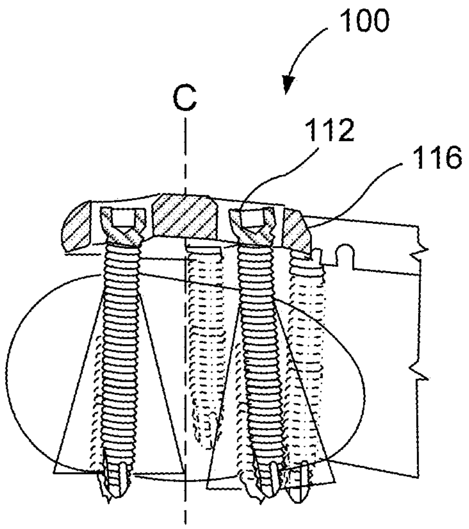
FIG. 8 shows another cross-sectional perspective view of a lateral portion of the first lateral plate of FIG. 3.

As shown in FIG. 8, one or more of these variable angle holes may diverge away from the central plane C, extending along a central axis angled with respect to the central plane C at an angle of up to 5 degrees so that central axis intersects with the central plane proximally of the upper surface 108. In one embodiment, a posterior one of the variable angle holes shown in FIG. 8 extends along a central axis substantially parallel to the central plane C while an anterior one of the variable angle holes shown in FIG. 8 extends along a central axis that diverges away from the central plane C. Although the plate 100 is specifically shown and described as having variable angle holes 112 positioned relative to one another in a specific configuration, it will be understood by those of skill in the art that the first portion 116 may include any number of variable angles holes 112 positioned relative to one another in any of a variety of configurations so long as bone screws are insertable therethrough into varying portions of a lateral fragment of the clavicle.

Figure 9:
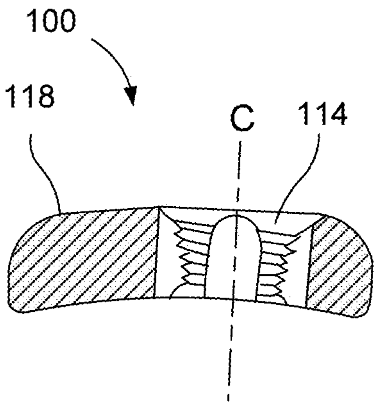
FIG. 9 shows a cross-sectional view of a medial portion of the first lateral plate of FIG. 3.

A second portion 118 of the plate body 102 proximate the second end 106 includes the plurality of variable angle holes 114, each of the variable angle holes 114 extending therethrough from the upper surface 108 to the lower surface 110 along a central axis substantially perpendicular to the upper surface 108. The second portion 118 is configured to extend over a portion of the second section of the clavicle identified with respect to FIG. 1. In this embodiment, the central axis of a first one of the variable angle holes proximate the second end 106 extends through the plate body along the central plane C. The remaining variable angle holes 114 are staggered relative to one another about the longitudinal axis of the plate body 102. As shown in FIG. 9, the central axes of these variable angle holes are, in this embodiment, angled at approximately 5 degrees relative to the central plane C so that the central axes converge at a point distal of the lower surface 110. In one embodiment, the upper surface 108 may be curved about the longitudinal axis of the plate body 102 such that the central axes of the variable angle holes 114 may be substantially perpendicular to the upper surface 108. The variable angle holes 114 may be substantially similar to the holes 112, described above, and are configured to receive bone screws therethrough at a user-selected angle relative to the central axes within a predefined range of angulation as would be understood by those skilled in the art.

The plate 100 may further include one or more combination holes 122 extending through a middle portion 134 of the plate body 102 between the first portion 116 and the second portion 118. The combination hole 122 extends through the plate body 102 from the upper surface 108 to the distal surface and includes a first portion 124 configured as a variable angle hole and a second portion 126 configured as a compression hole. The middle portion 134 including the combination hole 122 is positioned along a portion of the plate body 102 which, when the plate 100 is in the operative position, is configured to extend over a coracoclavicular ligament.

The first lateral plate 100 may also include a plurality of suture holes 128 extending therethrough from the upper surface 108 to the lower surface 110. The suture holes 128 extend through a portion of the plate body 102 extending along the lateral edge 130 and along longitudinal sides 132. The suture holes 128 are configured to receive a needle for suturing the plate to tissue and/or for receiving k-wires for temporary fixation of the plate 100 to the bone as would be understood by those skilled in the art.

It will be understood by those of skill in the first lateral plate 100 may be inserted through a small percutaneous incision positioned along a clavicle as discussed above. The first portion 116 may then be positioned over a first (lateral) fragment of the bone while the second portion 118 is positioned over a second fragment of the bone, upon alignment of the first and second fragments. The plate body 102 is fixed to the bone via insertion of screws through the combination hole 122 and the variable angle holes 112, 114, as necessary. Screws may be inserted through small incisions in the skin.

Figure 10:
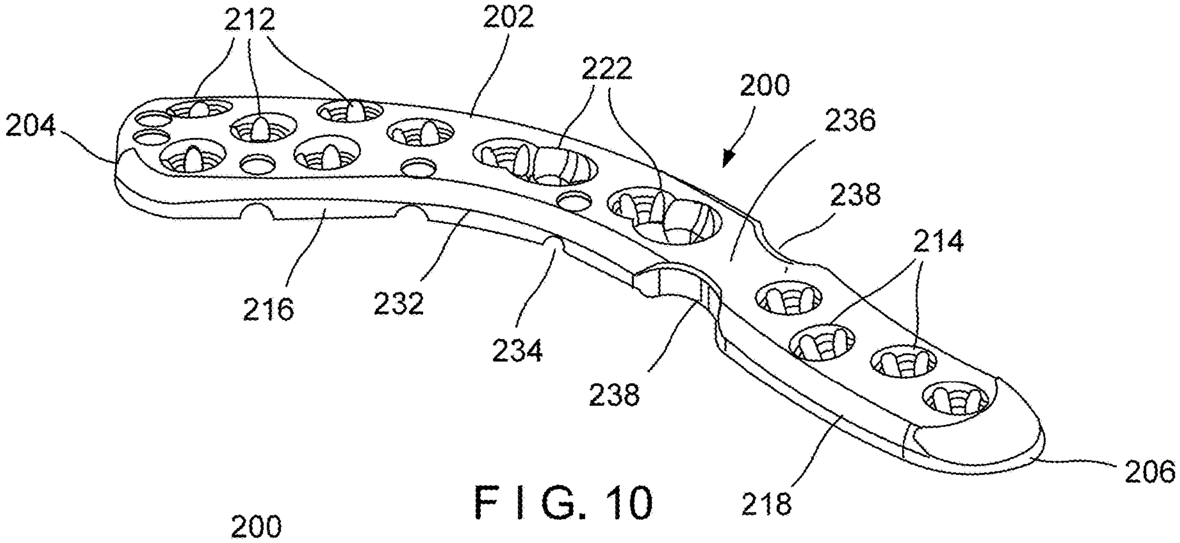
FIG. 10 shows a perspective view of a second lateral plate according to the system of FIG. 1.
Figure 11:
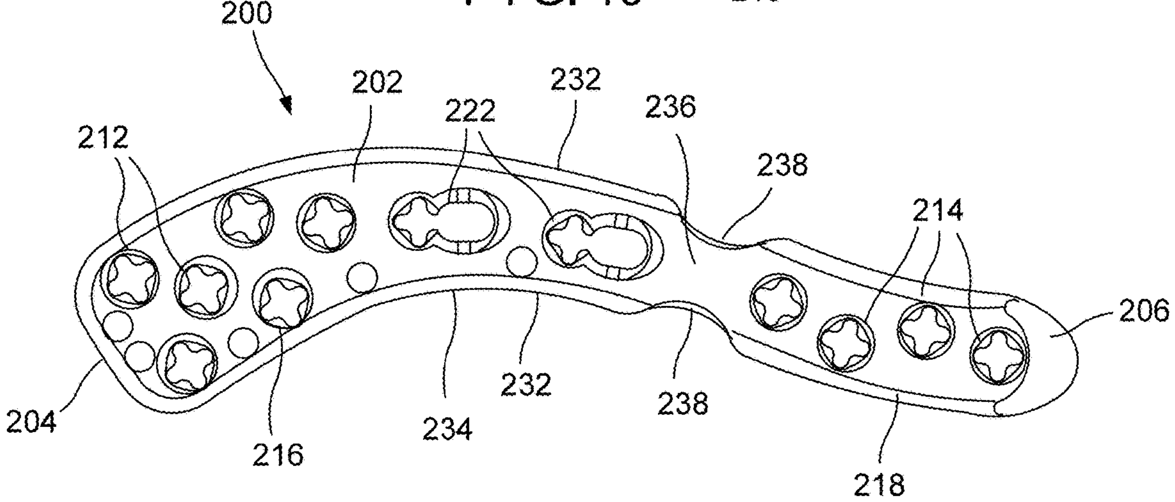
FIG. 11 shows a top plan view of the second lateral plate of FIG. 10.
Figure 12:
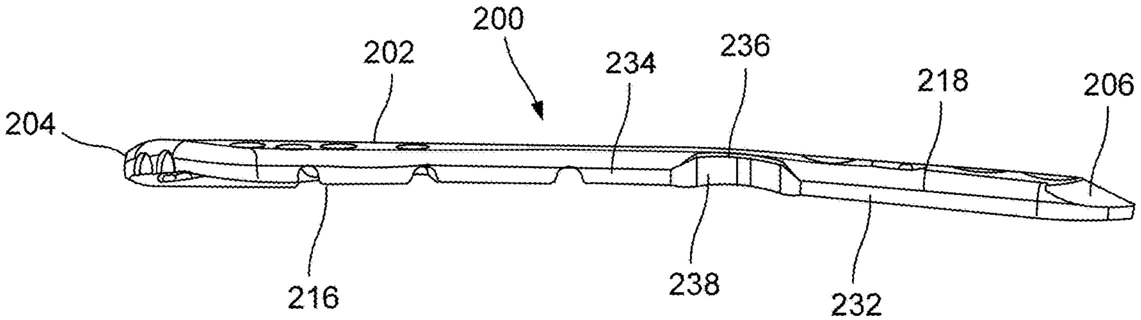
FIG. 12 shows a side view of the second lateral plate of FIG. 10.

As shown in FIGS. 10-12, a second lateral plate 200 may be substantially similar to the first lateral plate 100, but is sized, shaped and configured to treat larger clavicle bones than the first lateral plate 100 and/or for lateral fractures extending along a portion of the bone further from a lateral end of the bone. The second lateral plate 200 will include the same features as the first lateral plate 100, except as described below. Similarly to the first lateral plate 100, the second lateral plate 200 comprises a plate body 202 extending from a first end 204 to a second end 206.

A plurality of variable angle holes 212 extend through a first portion 216 of the plate body 202 proximate the first end 204 and a plurality of variable angle holes 214 extend through a second portion 218 of the plate body 202 proximate the second end 206. The plate body 202, however, may have a length ranging from approximately 70 mm to 100 mm. In one embodiment, the plate body 202 has a length ranging from approximately 75 to 95 mm and, in in a more particular embodiment, the length ranges from approximately 80 to 90 mm. Due to the longer length of the plate body 202 relative to the plate body 102, the plate 200 may include two combination holes 222 extending through a middle portion 234 of the plate body 202 between the first and second portions 216, 218.

The first portion 216 including the variable angle holes 212 and a middle portion 234 of the plate including the combination holes 222 extend along a curve corresponding to a lateral curve of a clavicle. In one embodiment, the first and middle portions 216, 234 have a radius of curvature of approximately 45 mm. The second portion 218 may, in an operative position, extend to a medial end of the second section of the clavicle, as identified in FIG. 1, so that the second portion 218 extends along a curve corresponding to a portion of a medial curve of the clavicle. In one embodiment, the second portion 218 extends along a curve having a radius ranging between approximately 75 mm and 85 mm. In one particular embodiment, the second portion 218 has a radius of curvature of approximately 80 mm. The second portion 218, in this embodiment, also includes a plurality of variable angle holes 214 staggered about the longitudinal axis of the plate body 202. In one embodiment, the second portion 218 includes four variable angle holes 214. It will be understood by those of skill in the art, however, that a number of variable angle holes 214 may vary depending on a length of the second portion 218 and/or a desired configuration of the variable angle holes 214 therealong.

The plate body 202 may also include a dedicated zone for in-plane bending to optimize a shape and configuration of the plate 200 for a patient=s specific anatomy. In other words, the plate body 202 may be bent in the same plane along which the plate body 202 extends. The zone for bending may be configured, for example, as a reduced width portion 236 of the plate body 202 extending between the middle portion 234 and the second portion 218, allowing the middle portion 234 and the second portion 218 to be bent with respect to one another. The reduced width portion 236 may include a pair of recesses 238 extending into longitudinal edges 232 of the plate body 202.

Figure 13:
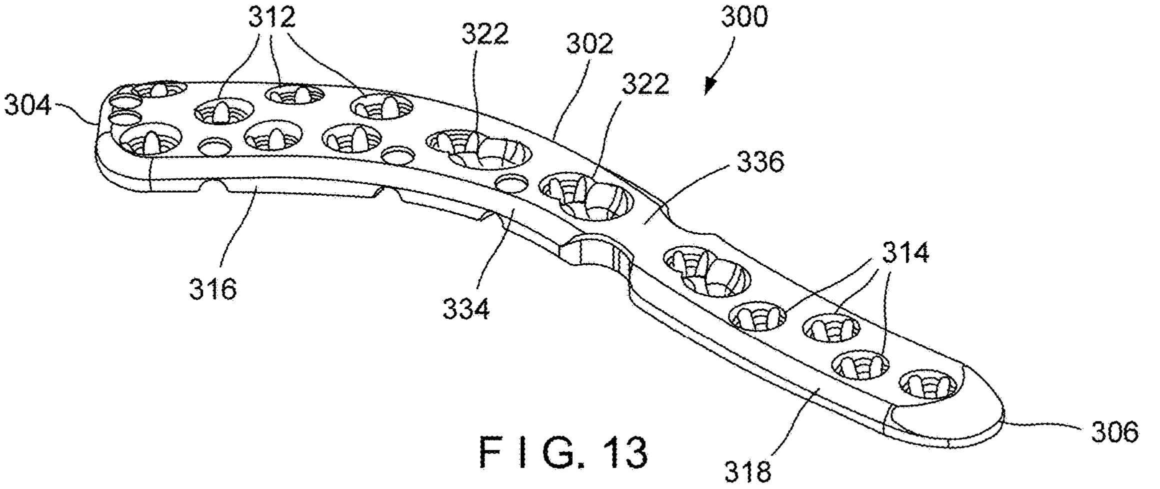
FIG. 13 shows a perspective view of a third lateral plate according to the system of FIG. 1.
Figure 14:
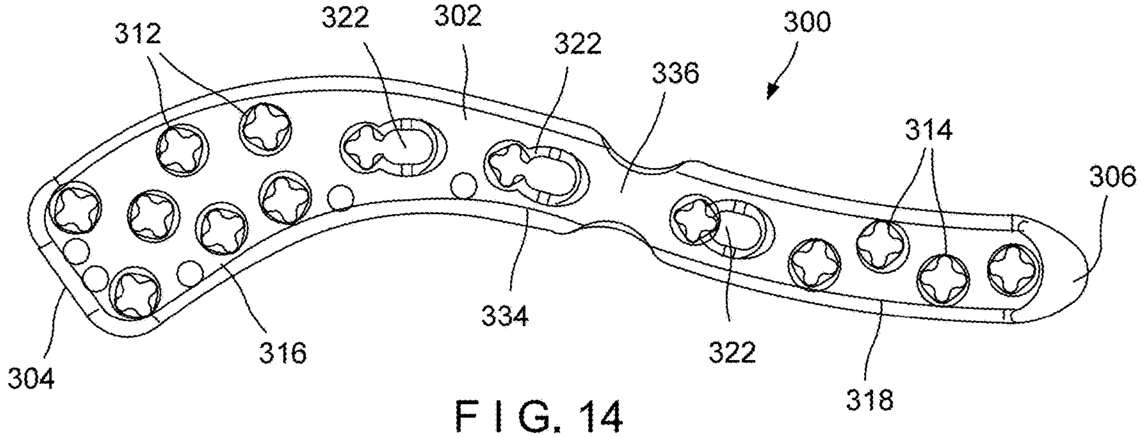
FIG. 14 shows a top plan view of the third lateral plate of FIG. 13.
Figure 15:
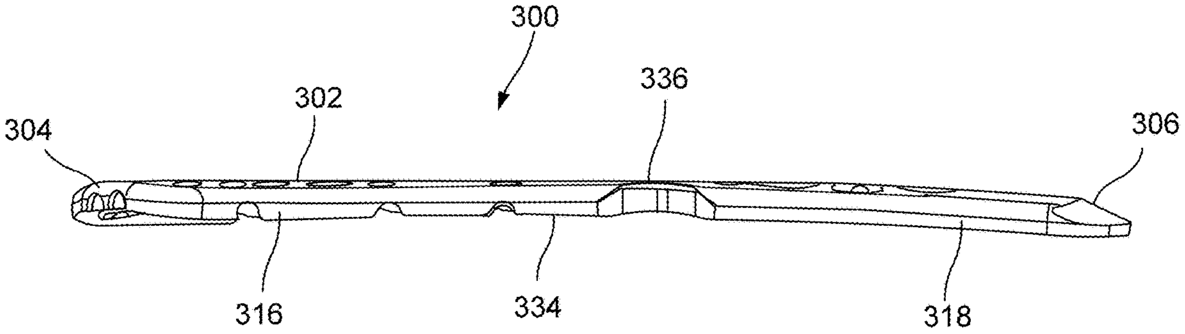
FIG. 15 show a side view of the third lateral plate of FIG. 13.

As shown in FIG. 13-15, a third lateral plate 300 may be substantially similar to the second lateral plate 200, but is dimensioned for a patient of larger stature. Similarly to the second lateral plate 200, a plate body 302 is configured to extend to a medial end of the second section of a clavicle, as identified in FIG. 1. In one embodiment, the plate body 302 may have a length ranging from approximately 80 mm to 110 mm. In another embodiment, the plate body 302 may have a length ranging from approximately 85 mm to 105 mm and, in a more particular embodiment, the plate body 302 may have a length of approximately 90 mm to 100 mm. A first end 304 of the plate body 302 may have a width of between 12 mm and 23 mm and, in a particular embodiment may have width of approximately 17-18 mm.

A first portion 316 and a middle portion 334 of the plate body 302, configured to extend along a lateral curvature of the clavicle, may have a radius of curvature of between approximately 44 mm to 54 mm and, in one particular embodiment, may have a radius of curvature of approximately 49 mm. A second portion 318, which is configured to extend along a portion of the medial curve within the second section, may, in one embodiment, may have a radius of curvature of between approximately 91 mm to 101 mm and, in one particular embodiment, may have a radius of curvature of approximately 96 mm.

Similarly to the second lateral plate 200, the first portion 316 includes a plurality of variable angle holes 312. The first portion 316, however, includes more variable angle holes 312 to accommodate the wider and longer plate body 302. The second portion 318 similarly includes variable angle holes 314 staggered about the longitudinal axis of the plate body 302. The second portion 318, however, further includes one or more additional combination holes 322 extending through a lateral end of the second portion 318 so that a bending zone 336 extending between the middle portion 334 and the second portion 318 extends between two adjacent combination holes 322.

It will be understood by those of skill in the art that one of the three lateral plates 100-300, as described above, may be selected for treating a patient based on a stature of the patient (e.g., dimensions of patient=s clavicle bone) and/or a location of a fracture along the bone. Although the exemplary embodiments specifically describe and show three lateral plates of various sizes and configurations, the system of the present disclosure may include more than three lateral plates for accommodating differently dimensioned clavicle bones.

The clavicle system of the present disclosure also includes shaft plates 400-700 for treating fractures along the second, third and/or fourth sections of the clavicle, as identified in FIG. 1. In particular, each of the shaft plates 400-600 is intended to treat fractures from along a medial portion of the second section to a medial end of the third section. Each of the three shaft plates 400-600 vary in size and shape to treat shaft fractures extending through clavicle bones of varying sizes. The shaft plate 700, may be specifically configured to treat extended fractures and is configured to extend along the fourth section of the clavicle. Extended fractures along small bones may also be treated using, for example, a medium shaft plate (e.g., plate 500) while extended fractures along medium bones may also be treated using a large shaft plate (e.g., plate 600).

Figure 16:
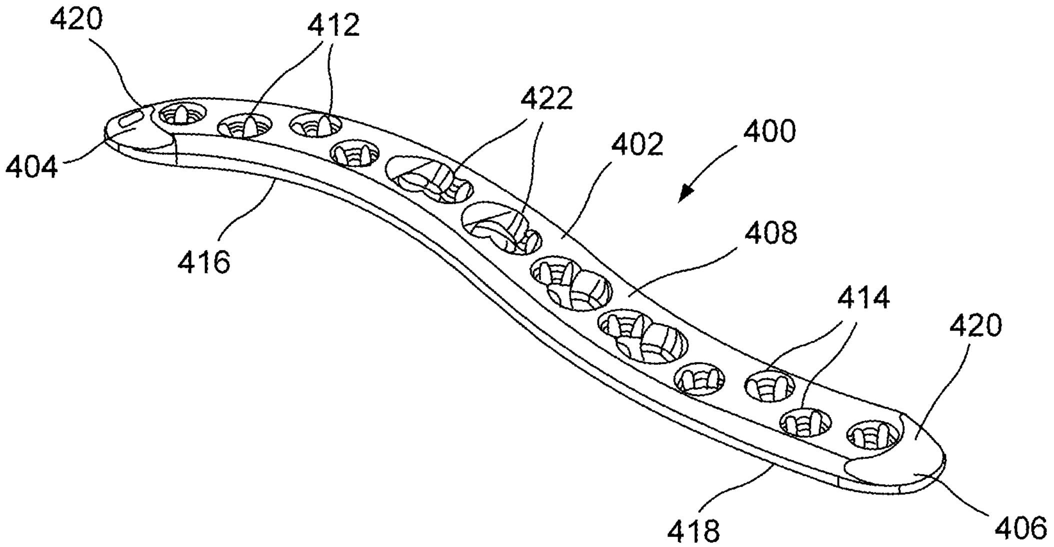
FIG. 16 shows a perspective view of a first shaft plate according to the system of FIG. 1.
Figure 17:
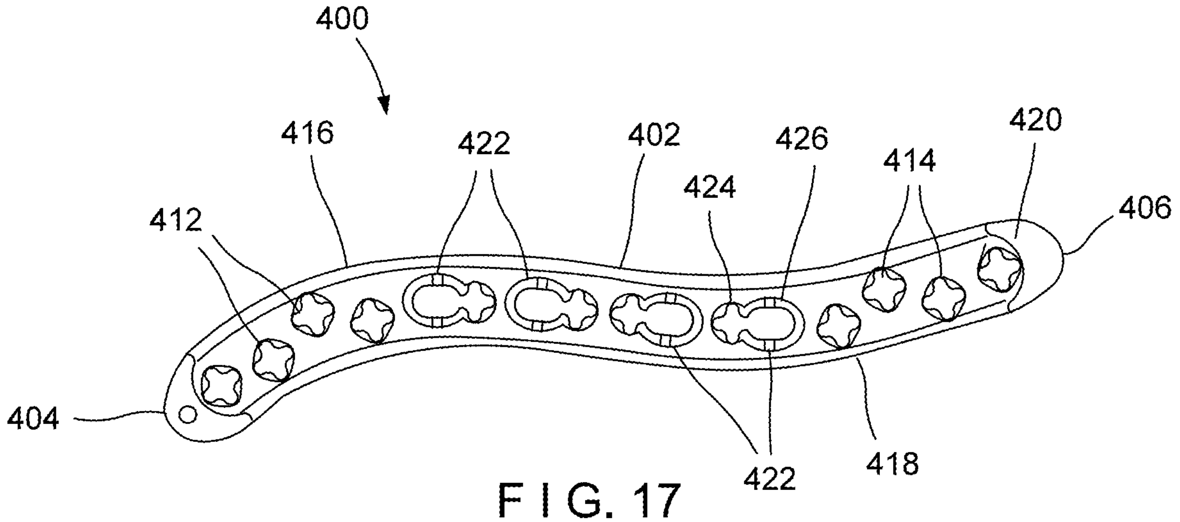
FIG. 17 shows a top plan view of the first shaft plate of FIG. 16.
Figure 18:
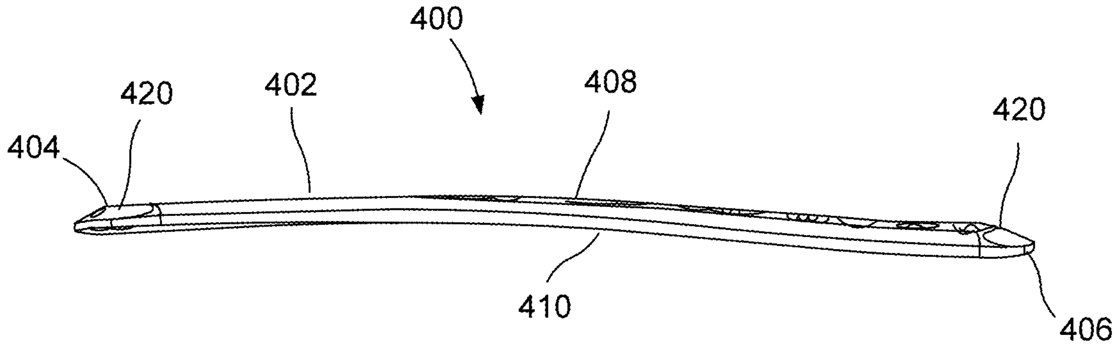
FIG. 18 shows a side view of the first shaft plate of FIG. 16.

As shown in FIGS. 16-18, a first shaft plate 400 comprises a plate body 402 extending from a first end 404 to a second end 406 and is defined via a proximal surface 408 which, in an operative position, faces away from a bone, to a distal surface 410 which, in the operative position, faces toward the bone. Similarly to the second ends of the lateral plates described above, both first and second ends 404, 406 of the plate body 402 includes an angled surface 420 connecting the proximal surface 408 to the distal surface 410, reducing a profile of the plate 400 at the second end 406 to facilitate insertion of the plate through a percutaneous insertion.

As described above, in the operative position, the plate body 402 extends along a portion of the second section of a clavicle bone to a medial end of the third section. In particular, the plate body 402 includes a first portion 416 that is sized, shaped and configured to extend along a portion of a lateral curve of a clavicle bone and a second portion 418 sized, shaped and configured to extend over a portion of a medial curve of the clavicle bone, when the plate 400 is in the operative position. As will be described in greater detail below, each of the first and second portions 416, 418 includes a first set of variable angle holes 412 and a second set of variable angle holes 414, respectively, along with combination holes 422 extending therethrough, from the proximal surface 408 to the distal surface 410.

In one embodiment, the plate body 402 may have a length ranging from approximately 80 mm to 115 mm. In another embodiment, the length of the plate body 402 may range from approximately 85 mm to 110 mm and, in a more particular embodiment, the length of the plate body 402 may range from 90 mm 105 mm. In one embodiment, the first portion 416 extends along a curve having a radius of curvature of between approximately 40 mm to 50 mm and, in a particular embodiment, the radius of curvature may be approximately 45 mm. The second portion 418 may extend along a curve having a radius of curvature of between approximately 70 to 80 mm and, in one particular embodiment, may have a radius of curvature of 74 mm.

In one embodiment, the first portion 416 includes a first set of variable angle holes 412 extending therealong from the first end 404. A first one of the variable angle holes 412 proximate the first end 404 extends through the plate body 402 along a longitudinal axis thereof. Subsequent variable angle holes 412 may be staggered relative to one another, about the longitudinal axis. In one embodiment, the first portion 416 includes four variable angle holes 412. Similarly to the first portion 416, the second portion 418 may include a plurality of variable angle holes 414 extending therealong from the second end 406. A first one of the variable angle holes 414 proximate the second end 406 extends through the plate body 402 along the longitudinal axis. Subsequent variable angle holes 414 may be staggered relative to one another about the longitudinal axis. The first and second set of variable angle holes 412, 414 may be substantially similar to the variable angle holes 114 described above with respect to FIGS. 3-9. In particular, each of the holes 412, 414 extends along central axes angled relative to a central plane so that the central axes converge with the central plane distally of a distal surface 410.

The plate 400 also includes a plurality of combination holes 422 extending through the plate body 402 between the first and second set of variable angle holes 412, 414. In one embodiment, the plate 400 may include four combination holes 422. The combination holes 422 extend through the plate body 402 substantially along the longitudinal axis. In one embodiment, the configuration of holes along the first and second portions 416, 418 substantially mirror one another. In particular, the second portion 418 may similarly have four variable angle holes. In addition, combination holes 422 extending along the first portion 416 may have variable angle hole portions 424 extending medially of compression hole portions 426 while combination holes 422 extending along the second portion 418 may have variable angle portions 424 extending laterally of compression hole portions 426. It will be understood by those of skill in the art that first and second screws may thus be inserted initially through a combination hole 422 along the first portion 416 and a combination hole 422 along the second portion 418 to compress a fracture of the bone along which the plate 400 is implanted.

Figure 19:
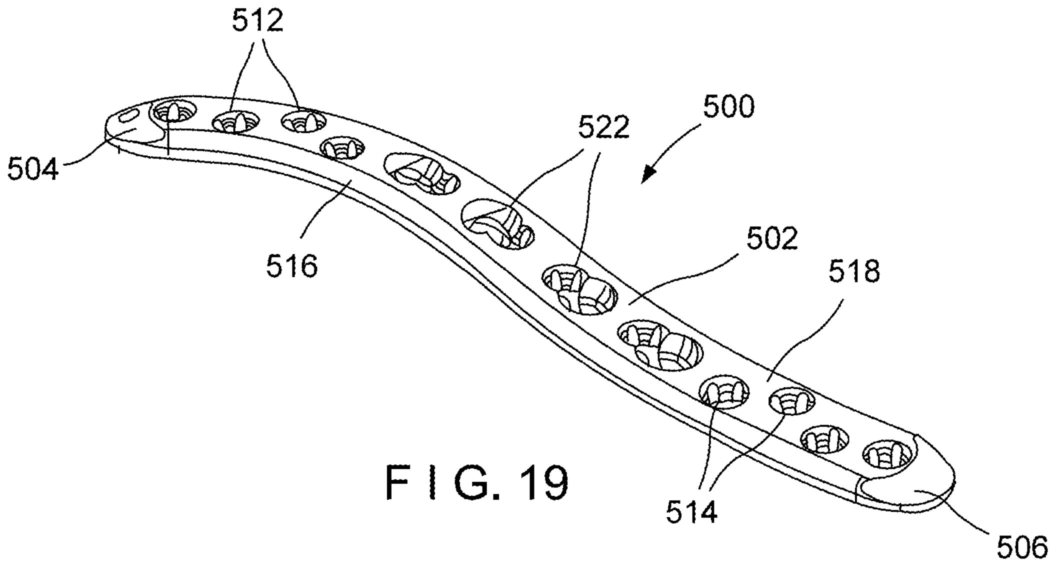
FIG. 19 shows a perspective view of a second shaft plate according to the system of FIG. 1.
Figure 20:
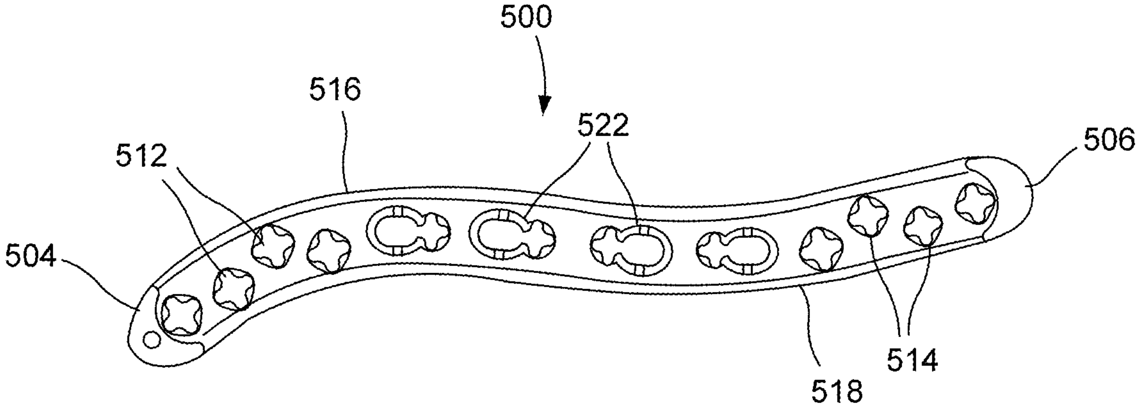
FIG. 20 shows a top plan view of the second shaft plate of FIG. 19.
Figure 21:
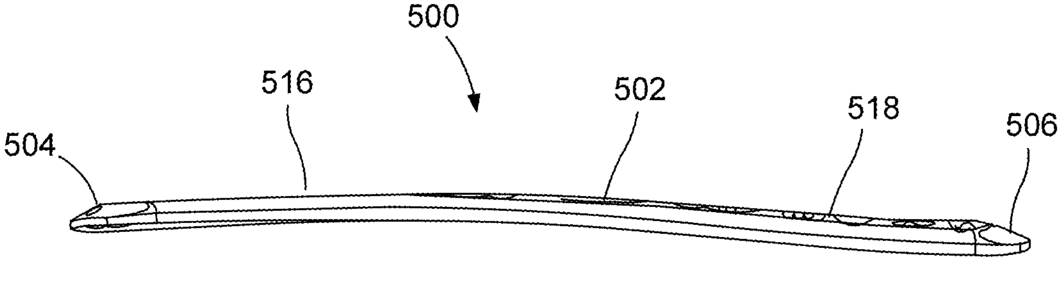
FIG. 21 shows a side view of the second shaft plate of FIG. 19.

A second shaft plate 500, as shown in FIGS. 19-21, may be substantially similar to the first shaft plate 400. The second shaft plate 500, however, is sized, shaped and configured to treat clavicle bones having larger dimensions than the first shaft plate 400. The second shaft plate 500 similarly comprises a plate body 502 including a first portion 516 configured to extend along a portion of a lateral curve of a clavicle and a second portion 518 configured to extend along a portion of a medial curve of the clavicle. The plate body 502, in this embodiment, has a length ranging from approximately 95 mm to 125 mm. In another embodiment, the length of the plate body 502 ranges from approximately 100 mm to 120 mm and, in a more particular embodiment, the length of the plate body 502 extends between approximately 105 mm and 115 mm.

The first portion 516 extends along a curve having a radius of curvature of, in one embodiment, ranging between approximately 45 mm to 55 mm and, in one particular embodiment, having a radius of curvature of approximately 50 mm. The second portion 518 extends along a curve having a radius of curvature of, in one embodiment, between approximately 82 mm to 92 mm and, in one particular embodiment, having a radius of curvature of approximately 87 mm. The first and second set of variable angle holes 512, 514 along with the combination holes 522 extend through and along the first and second portions 516, 516 substantially similarly to the plate 400.

Figure 22:
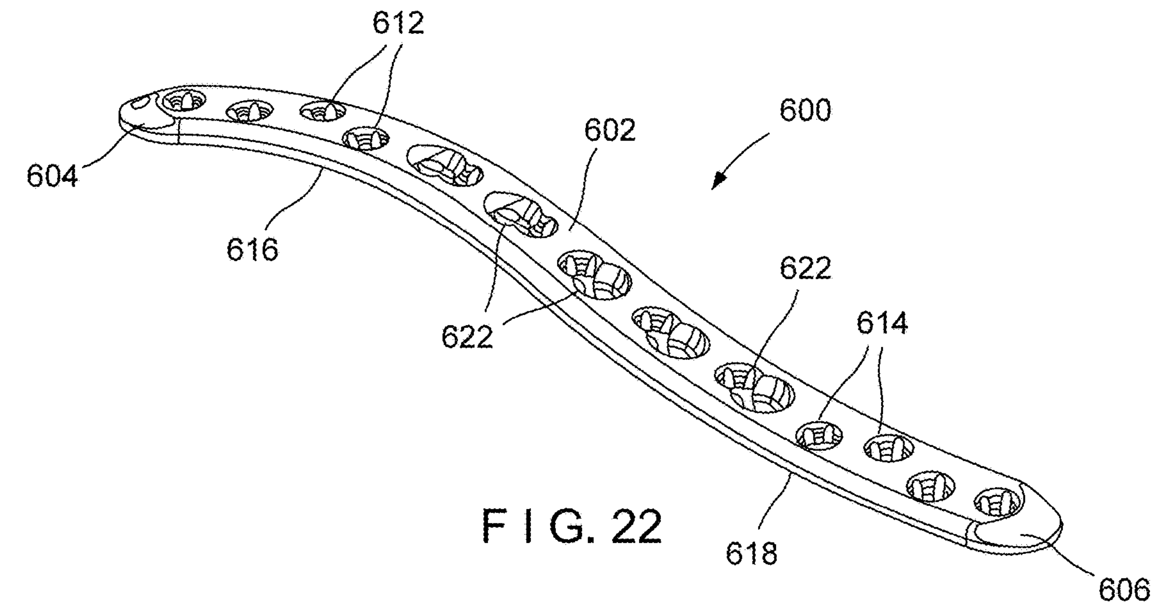
FIG. 22 shows a perspective view of a third shaft plate according to the system of FIG. 1.
Figure 23:
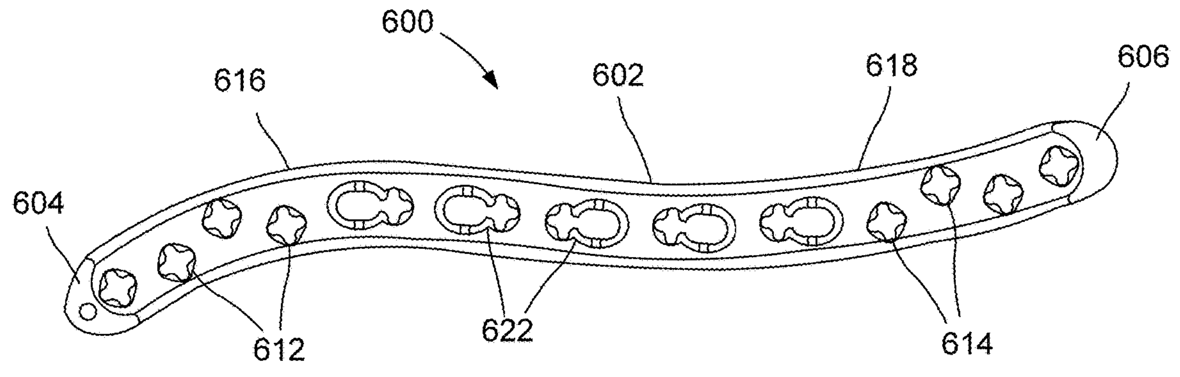
FIG. 23 shows a top plan view of the third shaft plate of FIG. 22.
Figure 24:
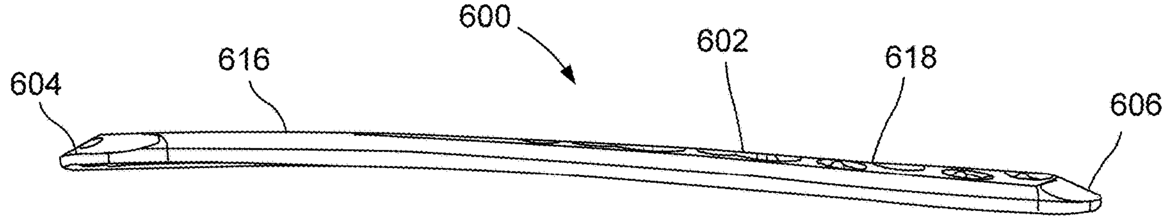
FIG. 24 shows a side view of the third shaft plate of FIG. 22.

A third shaft plate 600, as shown in FIGS. 22-24, may be substantially similar to the first and second shaft plates 400, 500, but may be particularly suited for patients having larger clavicle dimensions. Similarly, the third shaft plate 600 comprises a plate body 602 including a first portion 616 configured to extend along a portion of a lateral curve of a clavicle while a second portion 618 is configured to extend along a portion of a medial curve of the clavicle. The plate body 602, in this embodiment, may have a length ranging between approximately 110 mm to 140 mm. In a particular embodiment, the length of the plate body 102 may range between approximately 125 mm and 135 mm and, in a more particular embodiment, may range between approximately 120 mm and 130 mm.

The first portion 616 extends along a curve having a radius of curvature which, in one embodiment, ranges between approximately 54 mm to 64 mm and, in another more particular embodiment, has a radius of curvature of approximately 59 mm. The second portion 618 extends along a curve having a radius of curvature which, in one embodiment, ranges between 93 mm and 103 mm and, in a more particular embodiment, has a radius of curvature of approximately 98 mm. The third shaft plate 600 similarly includes first and second sets of variable angle holes 612, 614 along with combination holes 622 extending through first and second portions 616, 618. The third shaft plate 600, however, includes additional holes 612, 614, 622 to cover the longer length of the plate body 602.

Figure 25:
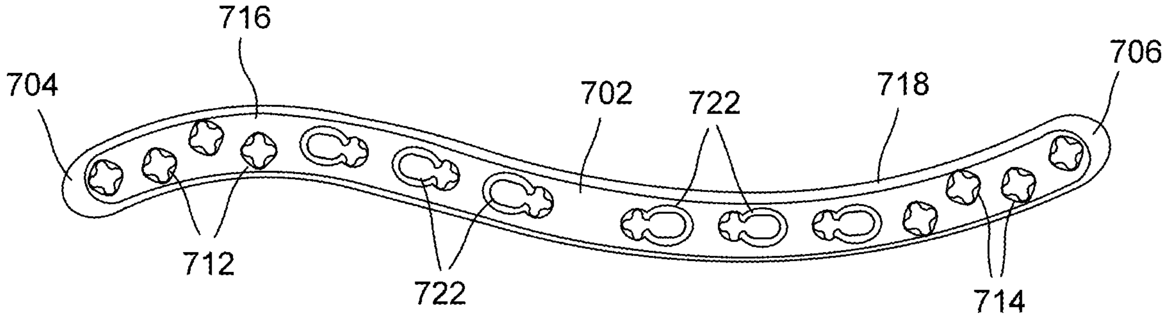
FIG. 25 shows a top plan view of a fourth shaft plate according to the system of FIG. 1.
Figure 26:
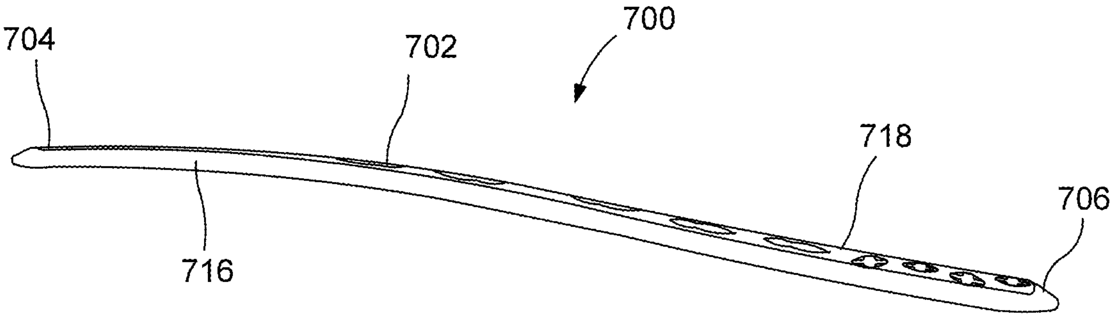
FIG. 26 shows a side view of the fourth shaft plate of FIG. 25.

A fourth shaft plate 700, as shown in FIGS. 25-26, may be substantially similar to the shaft plates 400-600. In particular, the fourth shaft plate 700 comprises a plate body 702 shaped similarly to the plate body 602, having substantially similar radii of curvature along first and second portions 716, 718. The plate body 702, however, has a longer length specifically designed to accommodate extended shaft fractures. In one embodiment, the fourth shaft plate 700 is configured to extend along a portion of a second section of a clavicle to a medial end of a fourth section of the clavicle, as shown in FIG. 1. In this embodiment, the plate body 702 may have a length ranging from approximately 130 mm to 160 mm. In another embodiment, the length of the plate body 702 may range from approximately 135 mm to 155 mm and, in a more particular embodiment, ranges between approximately 140 mm and 150 mm.

Figure 27:
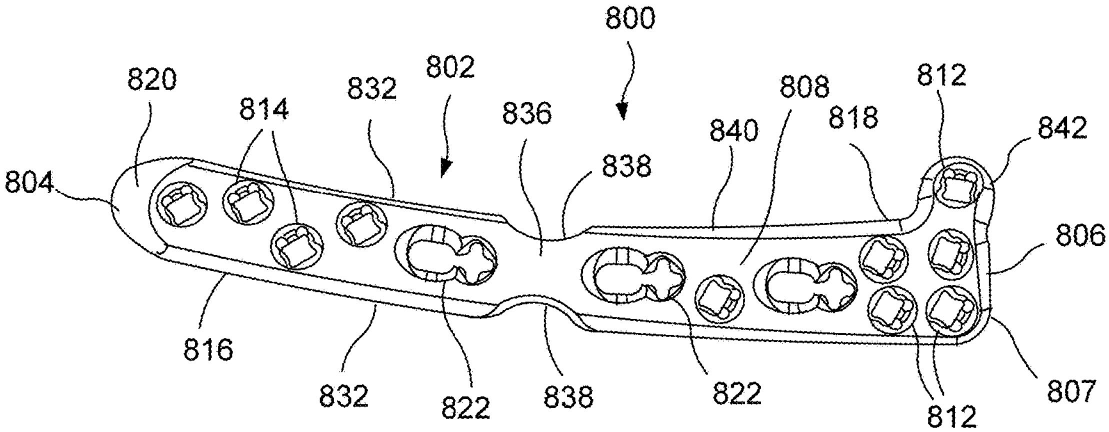
FIG. 27 shows a top plan view of a medial plate according to the system of FIG. 1.
Figure 28:
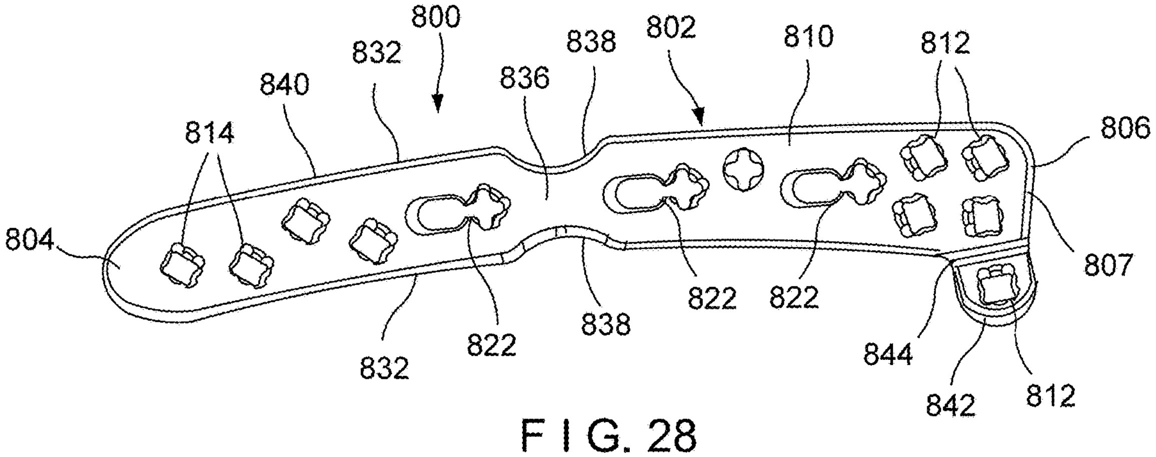
FIG. 28 shows a bottom plan view of the medial plate of FIG. 27.
Figure 29:
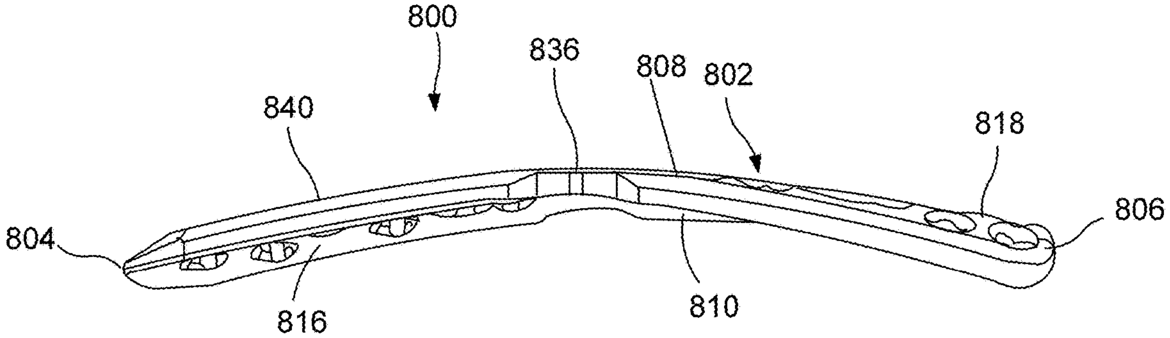
FIG. 29 shows a side view of the medial plate of FIG. 27.

As described above, conventional clavicle systems do not include designated medial plates. Medial fractures are currently often treated using off-label plates such as, for example, distal humerus plates and distal radius plates which, in some cases, do not provide an optimal fit over the clavicle. As shown in FIG. 27-29, the medial plate 800 is specifically sized, shaped and configured to treat medial fractures of a clavicle. The medial plate 800 comprises a plate body 802 extending from a first end 804 to a second end 806 and being defined via a proximal surface 808 which, in an operative position, faces away from a clavicle bone, and a distal surface 810 which, in the operative position, faces toward the clavicle.

The plate body 802 is sized and shaped so that, in the operative position, the second end 806 extends over an anterior surface of the medial end of the clavicle and a length of the plate body 802 extends through a fifth section of the clavicle and along a portion of a fourth section of the clavicle toward a superior surface. Thus, as shown in FIG. 29, the first end 804 of the plate body 802 is rotated about a longitudinal axis of the plate body 802 relative to the second end 806. The first end 804, in this embodiment, includes an angled surface 820 connecting the proximal surface 808 and distal surface 810 to form a low profile to facilitate insertion of the plate 800 through a percutaneous incision.

The plate body 802, in this embodiment, includes a longitudinally extending component 840 and an extension 842 extending from the second end 806 so that, when the plate 800 is in the operative position, the extension 842 extends toward a superior surface of the clavicle. The extension 842 extends transversely from the longitudinally extending component 840, away from a longitudinal axis of the longitudinally extending component 840. Along the distal surface 810 of the plate body 802, the plate 800 further includes a groove 844 extending between the extension 842 and the longitudinal component 840 so that the extension 842 may be bent relative to the longitudinal component 840 along the groove 844 to better suit the plate 800 to a patient=s specific anatomy.

The second end 806 of the plate body 802, including the extension 842, defines a second portion 818 of the plate body 802 through which a first set of variable angle holes 812 extends. In one embodiment, a first pair of variable angle holes 812 extend from the proximal surface 808 to the distal surface 810 proximate a medial edge 807 of the longitudinal component 840. Another variable angle hole 812 also extends through the extension 842 so that the variable angle holes 812 extending proximate the medial edge 807 and the extension are substantially aligned. A second pair of variable angle holes 812 is, in this embodiment, positioned immediately laterally of the first pair of variable angle holes 812. These variable angle holes 812 are configured to permit insertion of bone screws into the medial portion of the clavicle.

A second set of variable angle holes 814 extends along a first portion 816 of the plate body 802 including the first end 804. A first one of the variable angle holes 814 extends through the plate body 802 proximate the first end 804. A central axis of the first one of the variable angle holes 814 extends through a longitudinal axis of the plate body 802 and along a central plane extending through the longitudinal axis substantially perpendicular to the proximal surface 808. Similarly to the variable angle holes 114-714, the remaining variable angle holes 814 are staggered relative to one another about the longitudinal axis of the plate body 802 along the first portion 816 of the plate body 802. Combination holes 822 extend along a portion of the longitudinal component 840 of the plate body 802 extending between the first portion 816 and the second portion 818.

Similarly to the lateral plates 200-300, the medial plate 800 includes a bending zone 836 to facilitate bending of the plate body 802 to better suit a specific patient=s anatomy. The bending zone 836 in this embodiment is positioned between adjacent combination holes 822 and is formed, for example, as a reduced width portion defined via a pair of recesses 838 extending into longitudinal sides 832 along the longitudinal component 840. Although a single medial plate 800 is described and shown, it will be understood by those of skill in the art that the system of the present disclosure may include more than one medial plate, each of the medial plates having a different size, shape and/or configuration suited for treating patients with different bone dimensions.

According to an exemplary method of the system of the present disclosure, a user identifies a location of a clavicular fracture relative to one of the five sections, as described above with respect to FIG. 1. Based on the identification of the section, the user determines which plate type—e.g., lateral, shaft and/or medial—to use in treating the fracture. Once the user has determined a plate type to be used, a size of the identified plate type (e.g., lateral plates 100-300) may be selected based on a stature of the patient. To aid in identifying the size of plate to be used, the user may utilize a template, which is sized and shaped according to each available plate size, to determine whether the selected plate size would be a good fit for the patient.

It will be understood by those of skill in the art that although the exemplary embodiments show and describe plates having specific dimensions, the system of the present disclosure may include additional plates designed to include dimensions corresponding to bone dimensions of patients having varying statures. For example, although the exemplary embodiment describes basing the plates on a database of clavicle bones that were generally categorized into three categories—small, medium and larger—it will be understood by those of skill in the art that the system may include plates based on dimensions of bones that divided into more than three categories.

It will be understood by those of skill in the art that modifications and variations may be made in the structure and methodology of the present embodiment, without departing from the spirit or the scope of the embodiments. Thus, it is intended that the present embodiments cover the modifications and variations of these embodiments provided that the come within the scope of the appended claims and their equivalents.

What is claimed is:

1. A shaft plate for treating fractures of a central portion of a clavicle between lateral and medial portions thereof, the shaft plate comprising:

a plate body sized and shaped to be positioned along the central portion of the clavicle, the plate body extending from a first end to a second end along a curve selected to match, when the plate body is positioned in a desired location on the clavicle, a lateral curve of the central portion of the clavicle and a medial curve of the central portion of the clavicle, the second end being configured to be mounted over a medial part of the central portion of the clavicle, the plate body defined via an upper surface which, in an operative position, faces away from the clavicle, and a lower surface which, in the operative position, faces the clavicle, the plate body including, at the first end, a first angled surface connecting the upper and lower surfaces and at the second end, a second angled surface connecting the upper and lower surfaces, the plate body defining a longitudinal axis extending along a curved path through a length of the plate body;

a first set of screw holes extending through a lateral portion of the plate body including the first end of the plate body, each of the first set of screw holes extends through the plate body from the upper surface to the lower surface along a central axis so that a bone screw is insertable therethrough, wherein at least a first one of the first set of screw holes extends through the plate body on the longitudinal axis and a second one of the first set of screw holes is offset from the longitudinal axis toward one of side edges of the plate body; and a plurality of combination holes extending through the plate body, a first one of the combination holes being located on the lateral portion of the plate body so that, when the plate body is mounted on a bone in a desired position, the first combination hole is located medially of the first set of screw holes, each of the combination holes including a first portion configured to receive a locking bone screw and a second portion configured to receive a non-locking screw therein.

2. The shaft plate of claim 1, further comprising a third one of the first set of screws is offset from the longitudinal axis in a direction opposite the offset of the second one of the first set of screws.

3. The shaft plate of claim 1, wherein a second one of the combination holes is located on a medial portion of the plate body so that, when the plate body is mounted on a bone in a desired position, the second combination hole is located laterally of a second set of screw holes extending through the medial portion of the plate body including the second end of the plate body.

4. The shaft plate of claim 3, wherein a curve in the medial portion of the plate body has a radius of curvature from 70 mm to 80 mm.

5. The shaft plate of claim 3, wherein a curve in the medial portion of the plate body has a radius of curvature from 82 mm to 92 mm.

6. The shaft plate of claim 3, wherein a curve in the medial portion of the plate body has a radius of curvature from 93 mm to 103 mm.

7. The shaft plate of claim 1, wherein a curve in the lateral portion of the plate body has a radius of curvature from 40 mm to 50 mm.

8. The shaft plate of claim 1, wherein a curve in the lateral portion of the plate body has a radius of curvature of approximately 45 mm.

9. The shaft plate of claim 1, wherein a curve in the lateral portion of the plate body has a radius of curvature of approximately 74 mm.

10. The shaft plate of claim 1, wherein the first set of screw holes includes at least one variable angle hole configured so that a user can lock a screw in the variable angle hole of the first set of screw holes at a user selected angle.

11. The shaft plate of claim 10, wherein each of the first set of screw holes extends through the plate along a corresponding central axis, and wherein central axes of the first set of screw holes are oriented to converge toward the longitudinal axis beyond the lower surface of the plate body.

12. The shaft plate of claim 1, wherein the first one of the first set of screw holes extends through the plate body along a central axis within a central plane of the plate body.

13. The shaft plate of claim 1, wherein each of the combination holes includes a variable angle hole portion and a compression hole portion, wherein the plurality of combination holes comprises multiple combination holes in a lateral portion of the plate body, and wherein each of the combination holes located in the lateral portion of the plate body has a variable angle portion located medially of its compression portion.

14. The shaft plate of claim 1, wherein each of the combination holes includes a variable angle hole portion and a compression hole portion, wherein the plurality of combination holes comprises multiple combination holes in a medial portion of the plate body, and wherein each of the combination holes located in the medial portion of the plate body has a variable angle portion located laterally of its compression portion.

15. The shaft plate of claim 1, wherein the length of the plate body is between 80 mm and 115 mm.

16. The shaft plate of claim 1, wherein the length of the plate body is between 105 mm and 115 mm.

17. The shaft plate of claim 1, wherein a curve in the lateral portion of the plate body has a radius of curvature from 45 mm to 55 mm.

18. The shaft plate of claim 1, wherein the length of the plate body is between 125 mm and 135 mm.

19. The shaft plate of claim 1, wherein a curve in the lateral portion of the plate body has a radius of curvature from 54 mm to 64 mm.

20. A shaft plate for treating fractures of a central portion of a clavicle between lateral and medial portions thereof, the shaft plate comprising:

a plate body sized and shaped to be positioned along the central portion of the clavicle, the plate body extending from a first end to a second end along a curve selected to match, when the plate body is positioned in a desired location on the clavicle, a lateral curve of the central portion of the clavicle and a medial curve of the central portion of the clavicle, the second end being configured to be mounted over a medial part of the central portion of the clavicle, the plate body defined via an upper surface which, in an operative position, faces away from the clavicle, and a lower surface which, in the operative position, faces the clavicle, the plate body including, at the first end, a first angled surface connecting the upper and lower surfaces and at the second end, a second angled surface connecting the upper and lower surfaces, the plate body defining a longitudinal axis extending along a curved path through a length of the plate body;

a first set of screw holes extending through a lateral portion of the plate body including the first end of the plate body, each of the first set of screw holes extends through the plate body from the upper surface to the lower surface along a central axis so that a bone screw is insertable therethrough, wherein at least a first one of the first set of screw holes extends through the plate body on the longitudinal axis and a second one of the first set of screw holes is offset from the longitudinal axis toward one of side edges of the plate body; and a plurality of combination holes extending through the plate body, a first one of the combination holes being located on the lateral portion of the plate body so that, when the plate body is mounted on a bone in a desired position, the first combination hole is located medially of the first set of screw holes, each of the combination holes including a first portion configured to receive a locking bone screw and a second portion configured to receive a non-locking screw therein, wherein a second one of the combination holes is located on a medial portion of the plate body so that, when the plate body is mounted on the bone in a desired position, the second combination hole is located laterally of a second set of screw holes extending through the medial portion of the plate body including the second end of the plate body; and wherein at least a first one of the second set of screw holes extends through the plate body on the longitudinal axis and a second one of the second set of screw holes is offset from the longitudinal axis toward one of the side edges of the plate body.

21. The shaft plate of claim 20, wherein the first one of the first set of screw holes extends through the plate body along a central axis within a central plane of the plate body.

22. The shaft plate of claim 20, wherein each of the combination holes includes a variable angle hole portion and a compression hole portion, wherein the plurality of combination holes comprises multiple combination holes in a lateral portion of the plate body, and wherein each of the combination holes located in the lateral portion of the plate body has a variable angle portion located medially of its compression portion.

23. The shaft plate of claim 20, wherein each of the combination holes includes a variable angle hole portion and a compression hole portion, wherein the plurality of combination holes comprises multiple combination holes in a medial portion of the plate body, and wherein each of the combination holes located in the medial portion of the plate body has a variable angle portion located laterally of its compression portion.

* * * * *